(12) United States Patent
Prakash et al.

(10) Patent No.: US 7,925,468 B2
(45) Date of Patent: Apr. 12, 2011

(54) METHOD FOR CHARACTERIZING HIDING OF COATING COMPOSITIONS AND APPARATUS USED THEREFOR

(75) Inventors: Arun Prakash, West Chester, PA (US); John Paul Gallagher, Hockessin, DE (US); Roger Albert Karmes, North East, MD (US); Allan Blase Joseph Rodrigues, Bloomfield Hills, MI (US)

(73) Assignee: E.I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 11/999,672

(22) Filed: Dec. 5, 2007

(65) Prior Publication Data
US 2010/0305902 A1    Dec. 2, 2010

(51) Int. Cl.
*G01B 11/00*    (2006.01)

(52) U.S. Cl. ..................................................... 702/172
(58) Field of Classification Search ................... 702/172
See application file for complete search history.

*Primary Examiner* — Tung S Lau
(74) *Attorney, Agent, or Firm* — Sudhir G. Desbmukh

(57) ABSTRACT

The present invention is directed to an apparatus and a method that characterizes the hiding of coating compositions, such as automotive OEM and refinishes paints. The method is directed to sequentially storing in a computing device hiding data obtained by measuring the color difference (ΔRGB) in reflections of light and dark portions of target areas of a monotonic coating resulting from a coating composition applied over hiding test panel and by measuring coating thicknesses of the monotonic coating that correspond to the target areas, classifying the type of the hiding data, selecting fitting equations applicable to the classified hiding data, fitting the selected equation to match the classified hiding data and locating a hiding thickness on the monotonic coating that corresponds to the threshold value of the color difference at that location to determine the hiding thickness of the coating composition.

20 Claims, 10 Drawing Sheets

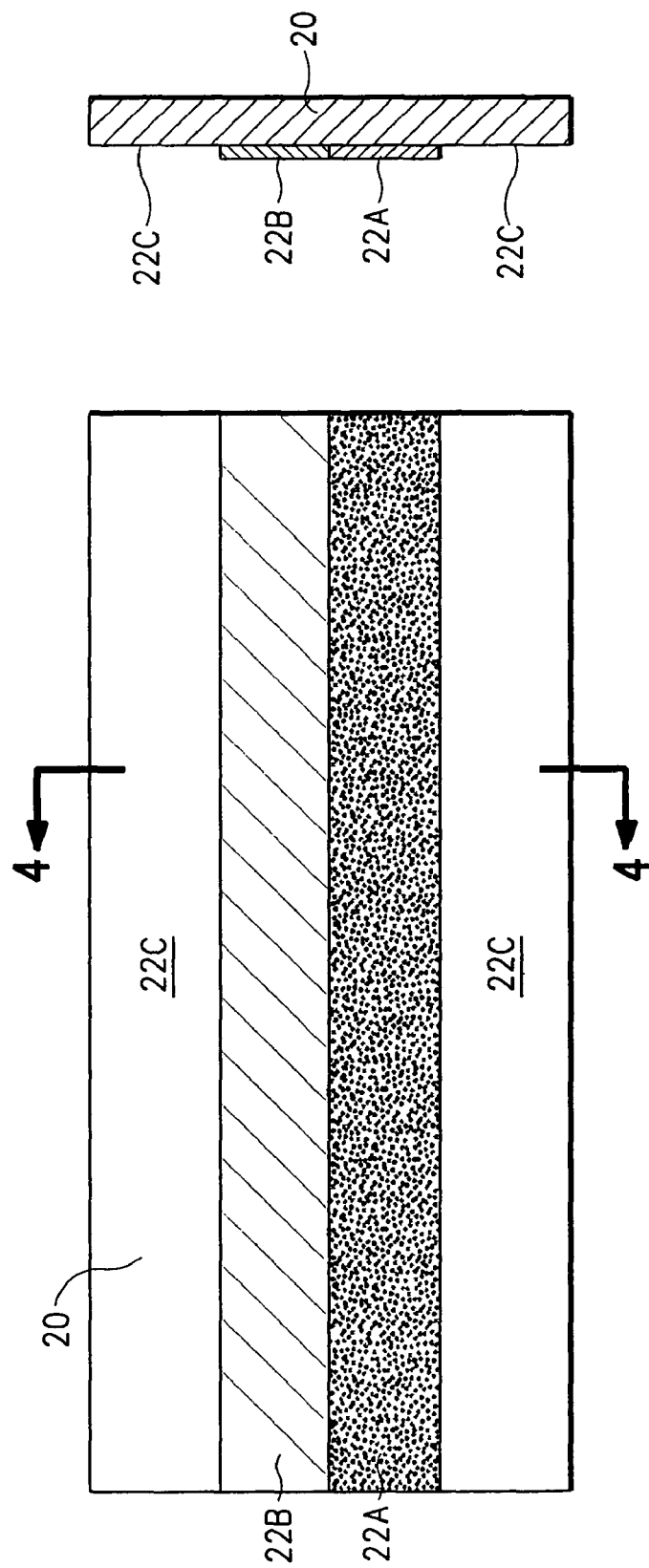

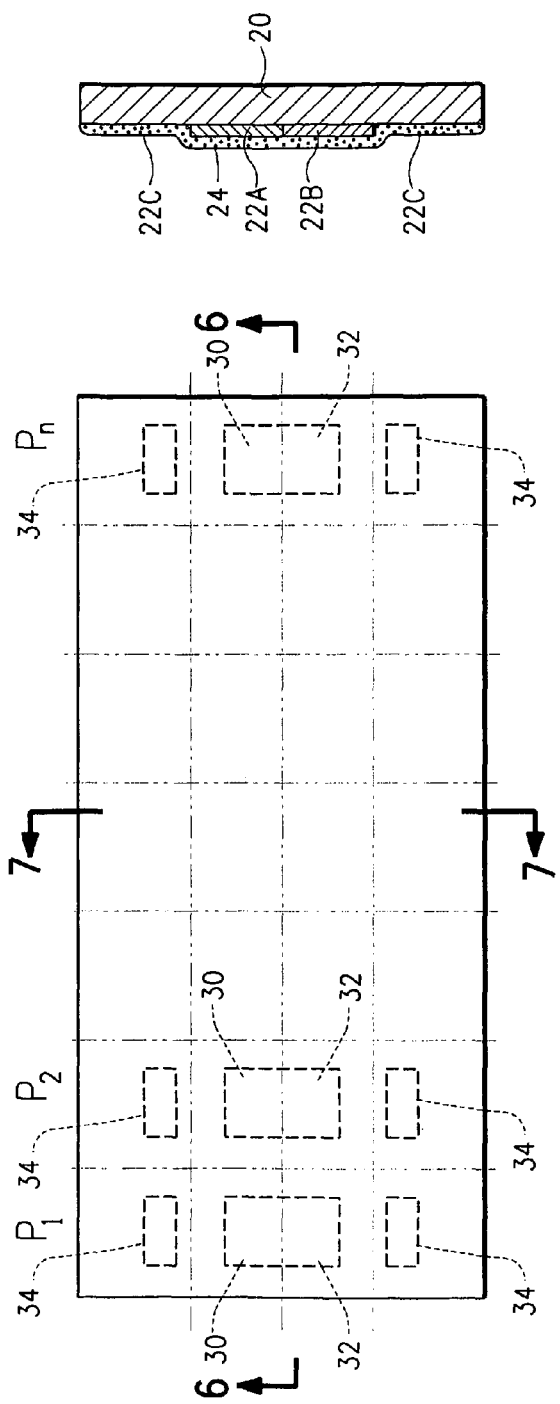
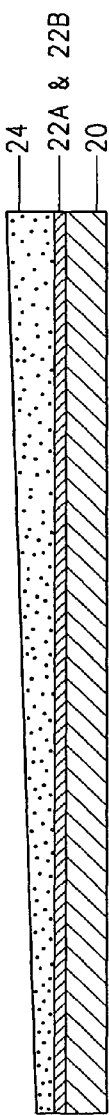
FIG. 5
FIG. 6
FIG. 7

100

┌─ 102
| Means for controlling first motion translating system 6 to sequentially direct reflections of light portion 30 and dark portion 32 target areas P1 to Pn of monotonic coating 24 to photosensitive device 8 to acquire intensities Ir1 to Irn, Ig1 to Ign and Ib1 to Ibn of light portions 30 of areas P1 to Pn, and intensities dr1 to drn, dg1 to dgn and db1 to dbn of dark portions 32 of areas P1 to Pn on monotonic coating 24 |

┌─ 104
| Means for controlling second motion translating system 10 to sequentially direct gage head 9 of a coating thickness detector 12 for measuring thicknesses X1 to Xn at locations 34 that respectively correspond to said target areas P1 to Pn |

┌─ 106
| Means for controlling time of exposure of a photo sensitive surface in photosensitive device 8 to the reflections of light portion 30 and dark portion 32 of target area P1 to attain highest contrast between light portion 30 and dark portion 32 of target area P1 |

FIG. 8

METHOD FOR CHARACTERIZING HIDING OF COATING COMPOSITIONS AND APPARATUS USED THEREFOR

FIELD OF INVENTION

The present invention is directed to an apparatus and a method used for characterizing hiding of coating compositions, such automotive paints.

BACKGROUND OF INVENTION

The hiding of a pigmented coating composition, such as an automotive OEM (original equipment manufacturer) paint or automotive refinish paint, is generally characterized by determining its hiding power, usually by visual observation. The hiding power is the measure of a coating composition's ability to cover a surface opaquely so that an underlying coating, such as that from a primer, cannot be seen in visible light. The absorption and scattering of incident light affects the hiding power of a coating composition. Thus, for example, the compositions of darker colors absorb more intensely than those of lighter colors and hence such compositions have greater hiding power than those of lighter colors.

Several methods for determining the hiding power of a coating composition are known in the coatings art. One such method (ASTM D 6762-02a) supplied by ASTM International, West Conshohocken, Pa.) consists of applying a monotonic, i.e., wedge shaped, layer of a coating composition over a test hiding pattern affixed to a hiding panel. After the applied layer cures or dries into a coating, then visually observing the coating under light at an angle perpendicular to the coating to determine a position on the coating where the test pattern is barely or no longer visible. The aforementioned test pattern is typically in the form of two abutting white and black stripes and the monotonic layer of increasing gradient is thinnest at one end of the test pattern and thickest at the other end of the test pattern. The monotonic coating is typically produced by progressively increasing the number of spraying passes over one end of the panel to the other. Typically, on one end of the panel, the test pattern is clearly visible through the coating (non-hiding end) whereas the test pattern is not visible at other end (hiding end). The hiding power of a coating composition is the lowest coating thickness at which hiding occurs. That would be the coating thickness at which the coating, such as paint, should be applied. Anything less will not be adequate and anything more would be a waste. The process for measuring the hiding power of a coating composition is currently done by technicians who visually examine the hiding panel and mark the position where the hiding pattern is no longer visually discernable. A film thickness gage is then used to measure the coating thickness at this position on the panel and recorded as the hiding film thickness for that particular coating. This approach is prone to significant errors because of visual subjectivity, due to variations in lighting used for observing the panel and observing geometry variation. Furthermore, the film thickness measured by a gage is very sensitive to the technique of usage and adds another significant source of error.

Some prior art references describe instruments for measuring color difference between two areas and when this difference goes below a pre-determined value, the coating thickness at that point would represent the hiding thickness of that coating composition. However, using the same pre-determined value to represent hiding for different colors and finishes does not produce the best results. For finishes that have high sparkle from metallic flakes, hiding occurs even with relatively high color difference whereas for solid colors, such as certain whites and yellows, hiding only occurs at extremely low values of color difference. Thus, using a single predetermined value does not produce accurate results. Furthermore, color and film thickness measurements on typically prepared hiding panels can have various random errors in them. Air bubbles under the hiding test pattern sticker, smudges and scratches, etc., can result in incorrect readings of color intensities. Similarly, the coating thickness measurements at any one point can have errors. Thus, most of the known methods fail since they have the aforedescribed errors. Thus, a need exits for a method and hiding measurement apparatus that is practical in that it is adaptive and error correcting and it accurately determines the hiding of various colors and coating compositions, including those that contain flakes, such as metallic, pearlescent, and mineral flakes The patent publication GB 1404 636 describes a system and a method for determining the hiding power of paints. According to the patent publication, a layer of paint is applied on a substrate with black and white regions. The substrate is illuminated with light, and the light reflected from the black and white regions of the substrate is captured by photoelectric cells. Potential difference measured by using photoelectric cells is considered to be proportional to the difference in reflective value of the black and white regions. Hiding power is presumed to be a function of the difference in the reflectance over the black and white regions. However, the patent publication only mentions a system and method for determining hiding power of paint. It is not directed to determining the hiding thickness at which the hiding occurs. Therefore, a need still exists for more accurately and consistently determining the hiding thickness of coating compositions, even on wet painted substrates.

STATEMENT OF INVENTION

The present invention is directed to a method of characterizing hiding of a coating composition, said method comprising:

(i) applying a monotonic layer of said coating composition over a test pattern affixed to a hiding test panel to produce a monotonic coating thereon;

(ii) sequentially uniformly illuminating target areas $P_1$ to $P_n$ of said monotonic coating, each said target area comprising a light portion and a dark portion;

(iii) sequentially directing reflections of said target areas $P_1$ to $P_n$ to a photosensitive device for acquiring:

(a) intensities $lr_1$ to $lr_n$, $lg_1$ to $lg_n$, and $lb_1$ to $lb_n$ of said light portions of said areas $P_1$ to $P_n$, and (b) intensities $dr_1$ to $dr_n$, $dg_1$ to $dg_n$, and $db_1$ to $db_n$ of said dark portions said areas $P_1$ to $P_n$;

(iv) sequentially measuring applied measured thicknesses $X_1$ to $X_n$ of said monotonic coating at locations that respectively correspond to said target areas $P_1$ to $P_n$;

(v) sequentially computing measured $Y_1$ to $Y_n$ at said target areas $P_1$ to $P_n$ by using the formula:

$$[(lr_i - dr_i)^2 + (lg_i - dg_i)^2 + (lb_i - db_i)^2]^{0.5} \quad (1)$$

wherein i ranges from 1 to n, and said measured $Y_1$ to $Y_n$ are measured $\Delta$RGBs;

(vi) storing on a computing device hiding data comprising said measured $Y_1$ to $Y_n$ and said applied thicknesses $X_1$ to $X_n$;

(vii) determining a threshold measured $Y_{th}$ by using the formula:

$$\text{measured } Y_{th} = \text{Log}_e(\text{measured } Y_{max}), \quad (2)$$

said measured Ymax being the maximum value within the range of said measured $Y_1$ to $Y_n$;

(viii) sequentially comparing said measured $Y_1$ through $Y_n$ to identify first measured $Y_q$ that is less than measured $Y_{th}$ wherein q falls within said range 1 to n;

(ix) computing a ratio (q/n) to classify said hiding data, wherein said is classified as:
- (a) type 1 hiding data when said ratio is in the range of 0.01 to less than 0.25,
- (b) type 2 hiding data when said ratio is in the range of 0.25 to less 0.35,
- (c) type 3 hiding data when said ratio is in the range of 0.35 to less 0.50, or
- (d) type 4 hiding data when said ratio is in the range of 0.50 to 1.00;

(x) selecting one or more fitting equations applicable for said type 1 hiding data, type 2 hiding data, type 3 hiding data or type 4 hiding data, wherein said fitting equations define a relationship between (y) and (x), said (y) being a fitted color difference that corresponds to said (x), which is a fitted thickness on a fitted curve generated by said one or more fitting equations;

(xi) fitting said one or more selected fitting equations to match paired measured $(X_1, Y_1)$ to paired measured $(X_n, Y_n)$, wherein said fitted curve has a fitted baseline value of $y_b$ at an asymptote of said fitted curve;

(xii) selecting a fitted threshold value $y_{th}$ above said fitted baseline value $y_b$, wherein said fitted threshold value $y_{th}$ is suited for said type 1 hiding data, type 2 hiding data, type 3 hiding data or type 4 hiding data; and (xiii) locating a hiding thickness $x_h$ of said coating composition that corresponds to said fitted threshold value $y_{th}$ on said fitted curve.

The present invention is also directed to an apparatus for characterizing hiding of a coating composition, said apparatus comprising:

(i) a light source for illuminating target areas $P_1$ to $P_n$ of a hiding test panel at a desired angle of incidence and light source intensity wherein each said target area comprises a light portion and a dark portion, said hiding test panel having a monotonic coating from said coating composition applied thereon;

(ii) a first motion translating system affixed to a bed of said apparatus, said first motion translating system comprising a first movable stage and a first mechanism for translating said first movable stage;

(iii) a fixture affixed to said movable stage to position said hiding test panel thereon;

(iv) a photosensitive system affixed to said bed of said apparatus, said photosensitive system being positioned to receive reflections of said light portion and said dark portion of each said target area of said hiding test panel;

(v) a second motion translating system affixed to said bed of said apparatus, said second motion translating system comprising a second movable stage and a second mechanism for translating said second movable stage in a direction perpendicular to that of said first movable stage;

(vi) a coating thickness detector affixed to said second movable stage for measuring thicknesses $X_1$ to $X_n$, at locations that respectively correspond to said target areas $P_1$ to $P_n$; and (vii) a computing device connected to said light source, said photosensitive system, said first and second motion translating systems and said coating thickness detector to direct steps performed by said light source, said photosensitive system, said first and second motion translating system and said coating thickness detector in accordance with a computer readable program code means stored in said computing device.

BRIEF DESCRIPTION OF DRAWING

FIG. 3 is a plan view of a hiding test panel on which a hiding pattern has been mounted.

FIG. 4 is a cross-sectional view of the hiding test panel of FIG. 3 taken along cross-section 4-4 in FIG. 3.

FIG. 5 is a plan view of a hiding test panel of FIG. 3 that has been coated with a monotonic coating.

FIG. 6 is a cross-sectional view of the coated hiding test panel of FIG. 5 taken along cross-section 6-6 in FIG. 5.

FIG. 7 is a cross-sectional view of the hiding test panel of FIG. 3 taken along cross-section 7-7 in FIG. 5.

FIG. 8 represents a flowchart that broadly illustrates and provides details of means for configuring computer readable program code means in the computing device for operating the apparatus of the present invention.

DETAILED DESCRIPTION OF PREFERRED THE EMBODIMENT

As defined herein:

Hiding test panel means a substrate over which the test pattern is preferably centrally affixed, such that a bare surface on the hiding panel is exposed on one or both sides of the test pattern. Substrate can be made of any conventional substrates, such as steel, aluminum, copper, wood, glass or plastic resin.

Figure 1:
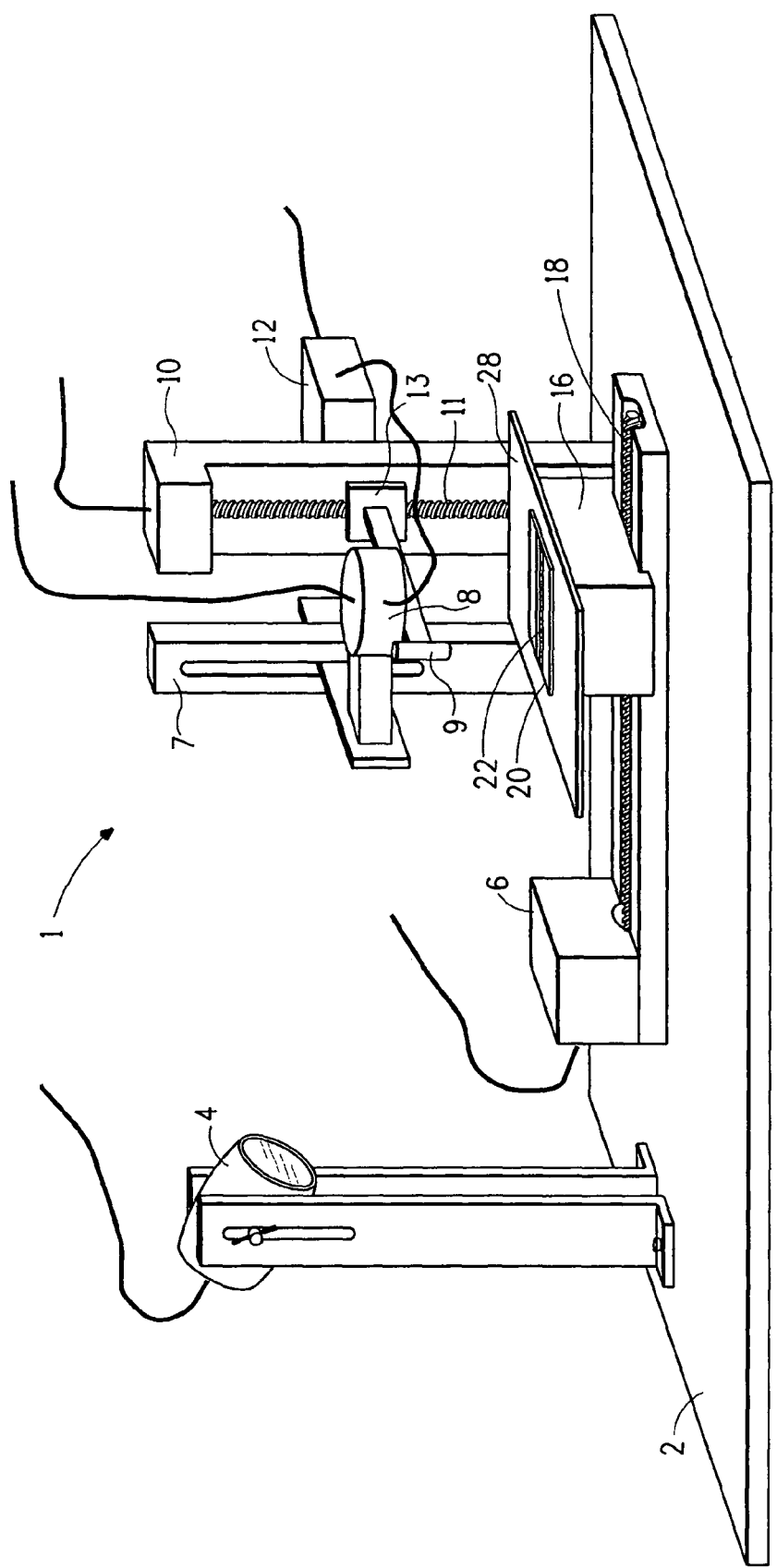
FIG. 1 broadly illustrates one of the embodiments of the apparatus of the present invention.
Figure 2:
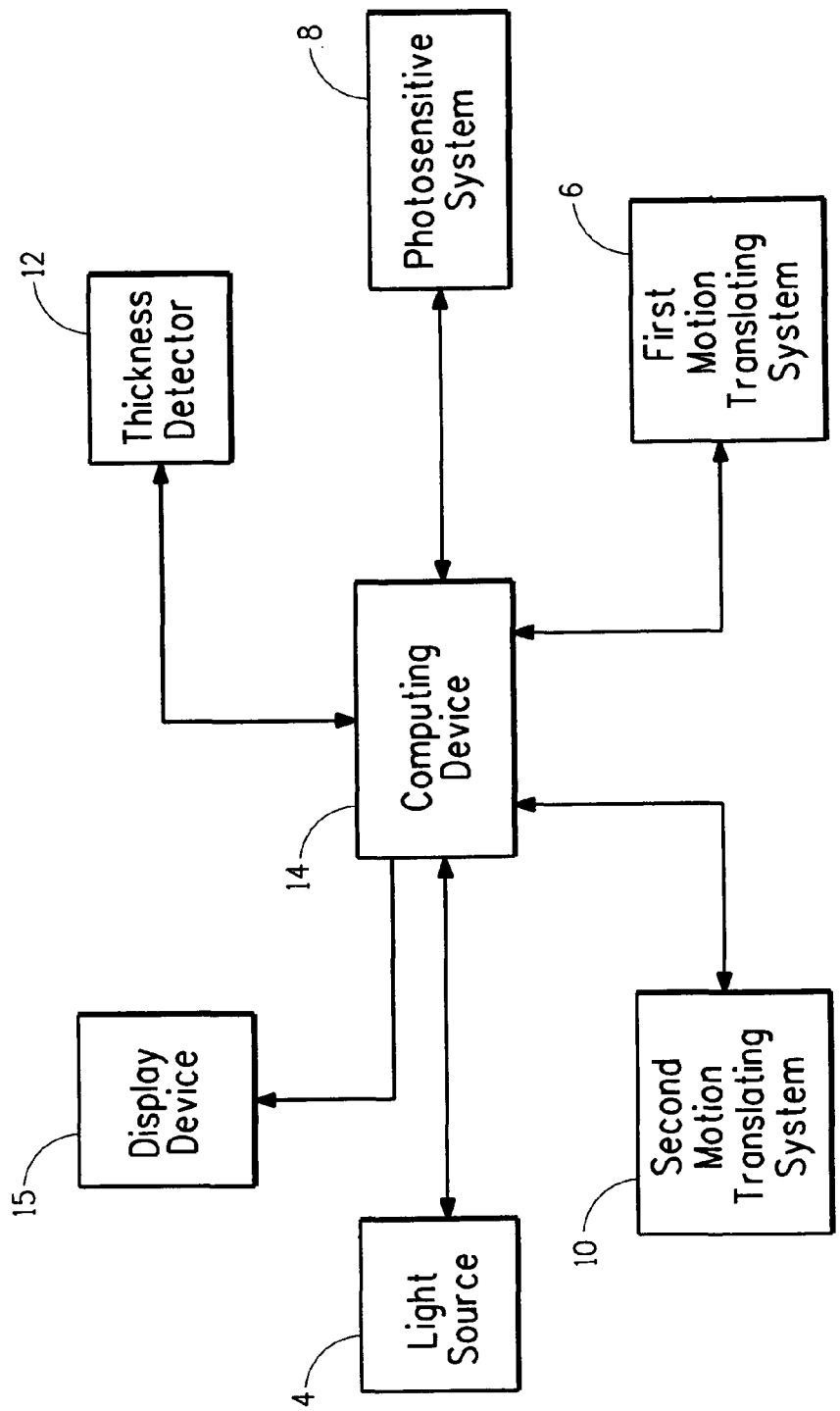
FIG. 2 provides the schematic presentation of how the various components of the apparatus of the present invention interact with a computing device.

As shown in FIGS. 1 and 2, major components of an apparatus 1 of the present invention for characterizing hiding of a coating composition includes a bed 2 having postioned thereon a light source 4, a first motion translating system 6, a photosensitive system 8, a second translating system 10, a coating thickness detector 12 and a conventional computing device 14, such as a Optiplex® GX620 Minitower computer supplied by Dell Computers of Round Rock, Tex. As shown in FIG. 2, computing device 14 is in communication with light source 4, photosensitive system 8, first motion translating 6 and second motion translating 10 systems and coating thickness detector 12. Computing device 14 is conventionally programmed in accordance with a computer readable program code means stored in computing device 14 to direct steps performed by light source 4, photosensitive system 8, first motion translating 6 and second motion translating 10 systems and coating thickness detector 12.

First motion translating system 6 is preferably affixed to bed 2 and includes a first movable stage 16 which can be translated by a first mechanism 18 for translating first movable stage 16 in one direction, preferably in a horizontal direction. First motion translating system 6 can be any suitable conventional system, such as Model Number MA2515 supplied by Velmax, Inc. of Rochester, N.Y.

FIG. 3 illustrates a typical hiding test panel 20 shown before it is coated. Test panel 20 can be made of any suitable substrate used for measuring hiding, such as metal, wood, glass, stone, fabric, or plastic. Metal substrate is preferred. Test panel 20 can have different shapes, such as rectangle, square, circle, oval, triangle, or irregular. Rectangular shape is preferred. Test panel 20 can be a flat surface, a curved surface, or a spherical surface. Flat surface is preferred. More preferably, test panel 20 is a 10.1 cm×30.5 cm (4"×12") flat rectangular metal plate. Test panel 20 is typically provided with a test pattern 22, which is typically a pattern with a pair of abutting stripes of contrasting colors, such as a dark stripe 22A and a light stripe 22B. Dark stripe 22A can be of any dark a color, such as black, red, or other dark colors. Black color is preferred. Light stripe 22B can be of any light color, such as white, gray, or other light color. White color is preferred. Dark and light stripes 22A and 22B are normally arranged as a pair such as, a black stripe abutting a white stripe, a black stripe abutting a gray stripe, or a red stripe abutting a gray stripe. Test pattern 22 is preferably centrally postioned on test panel 20 to expose a bare surface 22C on one or both sides of test pattern 22. A detailed description of a typical hiding pattern is provided in ASTM D 6762-02a (ASTM International in West Conshohocken, Pa. 19428).

As shown in FIGS. 5 and 6, a monotonic layer from a coating composition being tested for its hiding characteristic is conventionally applied, such as by spraying test pattern 22 on test panel 20. Upon cure, the monotonic layer applied over hiding panel 20 results into a monotonic coating 24, which is a wedge-shaped coating having a substantially ever increasing thickness that increase but never decreases from one end of test pattern 22 applied over hiding panel 20 to the other end of test pattern 22. Test pattern 22, typically made of an appropriately colored paper, film or coating that is adherent to the surface of hiding panel 20, would have some thickness, which can adversely affect the measurement of the coating thickness by apparatus 1. To eliminate such an error, monotonic coating 24, as shown FIGS. 5 and 6, also extends over locations 26 on exposed test panel surface 22C that are outside and alongside the surface of hiding panel 20 covered by test pattern 22. As shown in FIG. 1, hiding panel 20 is positioned in a positioning fixture 28 affixed to movable stage 16, preferably by providing panel 20 with notches in which matched detents located on fixture 28 can lock panel 20 firmly in place during the hiding measurements. It is contemplated that other suitable securing means for firmly securing panel 20 to fixture 28, such as magnets, clamps or a bezel frame are equally suitable for use in the present invention.

As seen in FIGS. 1, 2 and 5, light source 4 is used to uniformly illuminate target areas $P_1$ to $P_n$ of monotonic coating 24 on hiding test panel 20 at a desired angle of incidence and light source intensity. Target areas $P_1$ to $P_n$ are those areas on monotonic coating 24 that are sequentially illuminated by light source 4, viewed by photosensitive system 8 and analyzed by computing device 14. By way of example, a 10.1 cm×30.5 cm (4"×12") hiding test panel 20 can have 10 to 30 target areas, i.e., where n can range from 10 to 30 ($P_n$) at 1.27 cm (½") intervals by sequentially translating first movable stage 16 by means of first mechanism 18 at about 1.27 cm (½") intervals to expose target areas $P_1$ to $P_n$ on monotonic coating 24. As shown in FIG. 5, each target area would include a light portion 30 and a dark portion 32 that results from the underlying dark stripe 22A and light stripe 22B. Light source 4 can be any suitable conventional light source, such as SoLux® 40 watt, 4700 degree Kelvin, 17 degree spot solar simulator lamp supplied by, Tailored Lighting Inc. of Rochester, N.Y.

An adjustable post 7, which is preferably affixed to bed 2 is provided with means to secure photosensitive system 8 to sequentially receive reflections of paired light portion 30 and dark portion 32 of each target area $P_1$ through to $P_n$ on monotonic coating 24. One of such suitable photosensitive system 8 includes a video camera, such as model number GPUS522 supplied by Panasonic Systems Solutions Company of Secaucus, N.J. Preferably, photosensitive system 8 is postioned at 90 degrees to hiding test panel 20.

The distance between light source 4 and target areas $P_1$ to $P_n$ on monotonic coating 24 and the angle of incidence of light emanating from light source 4 typically control the uniformity of the illumination the target areas $P_1$ to $P_n$. Light source 4 is preferably postioned at an angle ranging from 5 degrees to 60 degrees to hiding test panel 20. The uniformity of illumination over target areas $P_1$ through to $P_n$ can be obtained by controlling the alignment of photosensitive system 8, monotonic coating 24 and light source 4. The aforedescribed alignment can be attained by providing various components of apparatus 1, such light source 4 and photosensitive system 8 with fine tuning adjustment means, such as micro-threaded set screws (not shown).

As seen in FIGS. 1, 2 and 5, second motion translating system 10 is preferably affixed to bed 2 apparatus 1. Second motion translating system 10 typically includes a second mechanism 11 for translating a second movable stage 13 in a direction perpendicular to that of first movable stage 16. Second motion translating system 10 can be any suitable conventional system, such as Model Number MA2509 supplied by Velmax, Inc. of Rochester, N.Y. A gage head 9 of a coating thickness detector 12 is affixed to a second movable stage 13 for measuring thicknesses $X_1$ to $X_n$ at locations 34 that respectively correspond to paired light portion 30 and dark portion 32 on each of target areas $P_1$ through to $P_n$. One of suitable coating thickness detector 12 that can be used in the present invention is CMI-213 Film thickness gage supplied by Oxford Instruments of Elk Grove, Ill.

As shown in FIGS. 5, 6, 7 and 8, computer readable program code means 100 of apparatus 1 of the present invention include means 102 for controlling first motion translating system 6 to sequentially direct reflections of light portion 30 and dark portion 32 of target areas $P_1$ to $P_n$ of monotonic coating 24 to photosensitive device 8 to acquire color intensities $lr_1$ to $lr_n$, in red color $lg_1$ to $lg_n$ in green color and $lb_1$ to $lb_n$ in blue color of light portions 30 of areas $P_1$ to $P_n$, and intensities $dr_1$ to $dr_n$, $dg_1$ to $dg_n$ and $db_1$ to $db_n$ of dark portions 32 of areas $P_1$ to $P_n$ on monotonic coating 24. These various color intensities, so called RGB (red, green and blue) intensities, are obtained by using appropriate red, blue and green filters in photosensitive system 8.

Means 100 can further include means 104 for controlling second motion translating system 10 to sequentially direct gage head 9 of a coating thickness detector 12 for measuring thicknesses $X_1$ to $X_n$ at locations 34 that respectively correspond to said target areas $P_1$ to $P_n$, typically on one or the other side of pattern 22.

As shown in FIG. 8, computer readable program code means 100 can include means 106 for controlling time of exposure of a photo sensitive surface in photosensitive device 8 to the reflections of light portion 30 and dark portion 32 of target area $P_1$ to attain highest obtainable contrast between light portion 30 and dark portion 32 of target area $P_1$ without saturating the photosensitive device anywhere else on the panel. Position $P_1$ of monotonic coating 24 at one end of test panel 20 is non-hiding, i.e., one can clearly see the underlying patterns 22A and 22B (no hiding) and position $P_n$ at the other end of test pattern 20 is completely hiding, i.e., one cannot see the underlying patterns 22A and 22B (total hiding). Means 106 are conventional items, such as timers for controlling exposure, switches, and aperture control needed to obtaining the desired degree of control of images of target area $P_1$ to P.

Typically, the intensities $lr_1$ to $lr_n$, $lg_1$ to $lg_n$ and $lb_1$ to $lb_n$ of light portions 30 and intensities $dr_1$ to $dr_n$, $dg_1$ to $dg_n$ and $db_1$ to $db_n$ of dark portions 32 and coating thicknesses $X_1$ to $X_n$ that correspond to target areas $P_1$ to $P_n$ are stored in computing device 14. As shown in FIG. 2, if desired, device 1 can include a display device 15, such as a computer monitor for viewing images of light portions 30 and dark portions 32 target areas $P_1$ to $P_n$.

In use, step (i) of a method of characterizing hiding of a coating composition includes applying a monotonic layer of the coating composition over test pattern 22 affixed to hiding test panel 20 to produce monotonic coating 24 thereon. The process for applying such a monotonic layer is well known. Typically, a coating composition, such as an automotive paint is successively sprayed in ever thicker layers from one end of hiding panel 20 to the other end. Upon cure, a monotonic coating 24 is produced on panel 20.

Step (ii) of the method of characterizing hiding of a coating composition includes sequentially uniformly illuminating target areas $P_1$ to $P_n$ of monotonic coating 24, wherein each target area includes light portion 30 and dark portion 32. Typically, light source 4 is adjusted to uniformly illuminate target area being analyzed. The distance from light source 4 to panel 20 is adjusted typically with set screws (not shown) for maximum obtainable light intensity and uniformity. If needed, the intensity of light source 4 can be also adjusted by conventional means, such as a rheostat. As shown in FIG. 2, most of the adjustments are preferably programmed through computing device 14. However, it is within the contemplation of the invention to use separate automated or manual conventional means for accomplishing the uniform illumination of target areas $P_1$ through to $P_n$.

Step (iii) of the method of characterizing hiding of a coating composition includes sequentially directing reflections of the target areas $P_1$ to $P_n$ to photosensitive device 8 for acquiring:

(a) intensities $lr_1$ to $lr_n$, $lg_1$ to $lg_n$ and $lb_1$ to $lb_n$ of light portions 30 of the areas $P_1$ to $P_n$, and (b) intensities $dr_1$ to $dr_n$, $dg_1$ to $dg_n$ and $db_1$ to $db_n$ of the dark portions 32 the areas $P_1$ to $P_n$.

The forgoing sequential measurements are accomplished by using first motion translating system 6.

Step (iv) of the method of characterizing hiding of a coating composition includes sequentially measuring applied measured thicknesses $X_1$ to $X_n$ of monotonic coating 24 at locations 34 that respectively correspond to the target areas $P_1$ to $P_n$. The forgoing sequential measurements are accomplished by using second motion translating system 10.

Step (v) of the method of characterizing hiding of a coating composition includes sequentially directing reflections of the target areas $P_1$ to $P_n$ to photosensitive device 8 for acquiring sequentially computing measured $Y_1$ to $Y_n$ at the target areas $P_1$ to $P_n$ by using the formula:

$$[(lr_i-dr_i)^2+(lg_i-dg_i)^2+(lb_i-db_i)^2]^{0.5} \quad (1)$$

wherein i ranges from 1 to n, and the measured $Y_1$ to $Y_n$, are measured $\Delta RGBs$. The aforedescribed steps (i), (ii), (iii), (iv) and (v) are further explained through Table 1 below, which, by way of example, shows one illustration of measuring color differences ($\Delta RGB$) $Y_1$ to $Y_n$ at target areas $P_1$ to $P_n$ by using apparatus 1 of the present invention. Color intensities $lr_1$ to $lr_n$, $lg_1$ to $lg_n$ and $lb_1$ to $lb_n$ of light portions 30 of areas $P_1$ to $P_n$, and intensities $dr_1$ to $dr_n$, $dg_1$ to $dg_n$ and $db_1$ to $db_n$ of dark portions 32 of areas $P_1$ to $P_n$ on monotonic coating 24 in red, green and blue colors, respectively were measured by using appropriate color filters on photosensitive system 8 and $\Delta RGBs$ were calculated by means of the aforedescribed equation (1). Coating thicknesses $X_1$ to $X_n$ corresponding to target areas $P_1$ to $P_n$ were measured by using coating thickness detector 12 of apparatus 1. The automotive applied on panel 20 was Imron® sparkling blue automotive paint supplied by Dupont Company of Wilmington, Del.

TABLE 1

| Target Areas $P_1$ to $P_n$ | CorresPonding coating 24 in cm | Corresponding Coating thickness $X_1$ to $X_n$ of coating 24 in microns | Color difference $\Delta RGBs$ |
|---|---|---|---|
| $P_1$ | 0.64 | 31.75 | 52.16 |
| $P_2$ | 1.91 | 32.00 | 46.04 |
| $P_3$ | 3.18 | 34.54 | 38.07 |
| $P_4$ | 4.45 | 34.29 | 30.3 |
| $P_5$ | 5.72 | 39.12 | 28.53 |
| $P_6$ | 6.99 | 41.66 | 23.36 |
| $P_7$ | 8.26 | 40.13 | 16.63 |
| $P_8$ | 9.53 | 42.67 | 16.93 |
| $P_9$ | 10.80 | 46.99 | 17.85 |
| $P_{10}$ | 12.07 | 54.10 | 7.48 |
| $P_{11}$ | 13.34 | 58.93 | 10.46 |
| $P_{12}$ | 14.61 | 60.20 | 3.23 |
| $P_{13}$ | 15.88 | 58.17 | 5.28 |
| $P_{14}$ | 17.15 | 59.18 | 4.44 |
| $P_{15}$ | 18.42 | 61.21 | 5.64 |
| $P_{16}$ | 19.69 | 67.31 | 2.86 |
| $P_{17}$ | 20.96 | 71.12 | 1.77 |
| $P_{18}$ | 22.23 | 73.91 | 1.55 |
| $P_{19}$ | 23.50 | 75.44 | 2.64 |
| $P_{20}$ | 24.77 | 75.18 | 2.26 |
| $P_{21}$ | 26.04 | 78.49 | 3.17 |
| $P_{22}$ | 27.31 | 86.36 | 2.16 |

Figure 9:
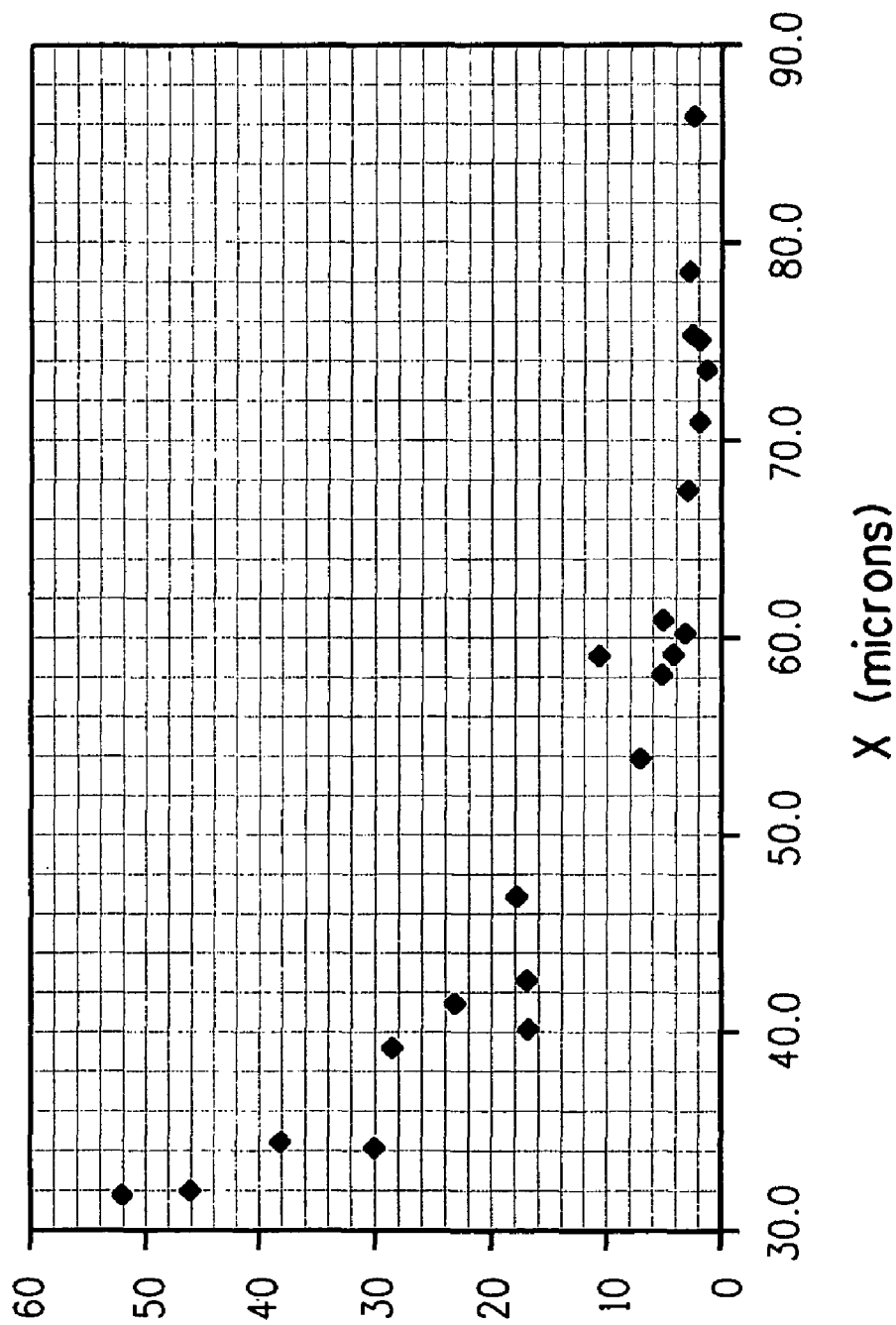
FIGS. 9 to 13 are various graphical renditions of ΔRGB (color difference between light and dark portions of the hiding pattern applied over the hiding test panel) versus the coating thickness of the monotonic coating applied over the test panel.

FIG. 9 shows a graphic representation of data in Table 1. As noted earlier, target area $P_1$ has the most contrast between light portion 30 and dark portion 32, i.e., a portion of monotonic coating 24 with least thickness (maximum $\Delta RGBs$) and $P_n$, wherein n equals 22 has the least contrast between light portion 30 and dark portion 32, i.e., a portion of monotonic coating 24 with most thickness (minimum $\Delta RGBs$). As the coating thickness of coating 24 on hiding pattern 22 increases from $P_1$ to $P_n$, the color difference ($\Delta RGB$) between the light portion 22A and dark portion 22B hiding pattern 22 on panel 20 decreases, and becomes less visible to the human eye. At a certain coating thickness somewhere between $P_1$ and $P_n$, the difference is no longer discernable to the human eye. That is the thickness at which the hiding occurs for that particular coating composition and such a thickness is called a "hiding thickness" for that particular coating composition. For different colors and finishes the point at which the color difference is no longer discernable varies. As a result, determining a hiding thickness from the measured $\Delta RGB$ data is more complex than simply measuring the color difference that falls below a single threshold $\Delta RGB$ value.

Step (vi) of the method of characterizing hiding of a coating composition includes storing on computing device 14 hiding data comprising the measured $Y_1$ to $Y_n$ and the applied thicknesses $X_1$ to $X_n$.

Step (vii) of the method of characterizing hiding of a coating composition includes determining a threshold measured $Y_{th}$ by using the formula:

$$\text{measured } Y_{th}=\text{Log}_e(\text{measured } Y_{max}), \quad (2)$$

the measured $Y_{max}$ being the maximum value within the range of the measured $Y_1$ to $Y_n$.

Step (viii) of the method of characterizing hiding of a coating composition includes sequentially comparing the measured $Y_1$ through $Y_n$ to identify first measured $Y_q$ that is less than measured $Y_{th}$ wherein q falls within said range 1 to n.

Step (ix) of the method of characterizing hiding of a coating composition includes computing a ratio (q/n) to classify the hiding data, wherein the hiding data is classified as:
- (e) type 1 hiding data when the ratio is in the range of 0.01 to less than 0.25,
- (f) type 2 hiding data when the ratio is in the range of 0.25 to less 0.35,
- (g) type 3 hiding data when the ratio is in the range of 0.35 to less 0.50, or
- (h) type 4 hiding data when the ratio is in the range of 0.50 to 1.00.

Figure 10:
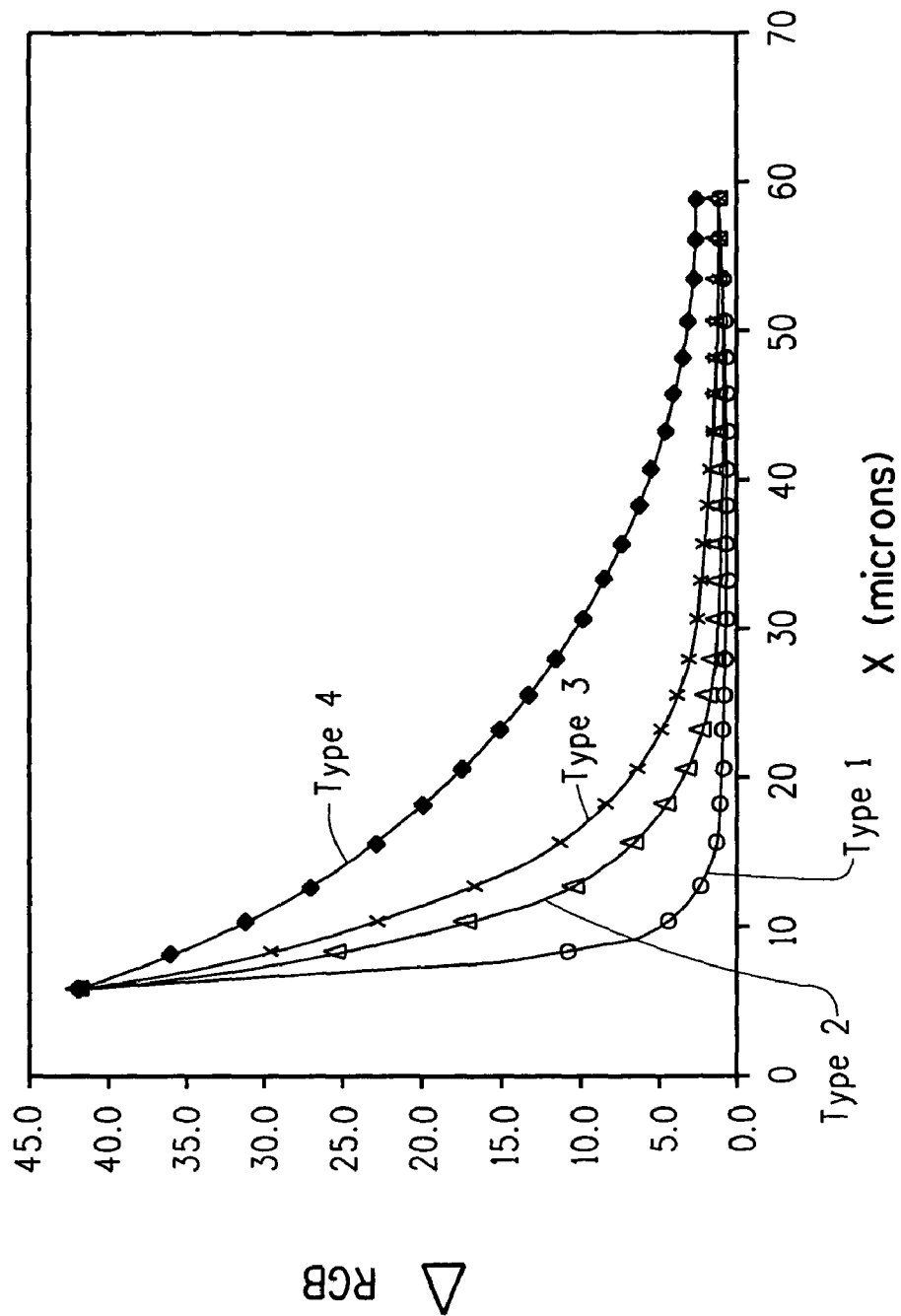

As provided in the aforementioned step (ix) above, the method of the present invention first classifies the measured ΔRGB data and then utilizes fitting functions to determine the hiding thickness. One can readily observe from FIG. 9 that individual measurements do not fall on a smooth curve, which results from instrumental and measurements errors that are inherent in typical measurement devices. Therefore, a need exists to develop a fitting model that would mathematically permit fitting the measured data on to a smooth curve. The present process applies a novel process to attain such a form fitting objective. Thus, in the aforementioned step (vii) a measured threshold $Y_{th}$ is first determined and then in the aforementioned step (viii) a first measured $Y_q$ is identified by sequentially comparing the measured $Y_1$ thorough to $Y_n$ to locate a first $Y_i$ that has a value less than the measured threshold $Y_{th}$, which is the first measured $Y_q$. Once the value "q" is identified then in the foregoing step (ix) a ratio of (q/n) is computed to classify the hiding data as type 1, wherein (q/n) is in the range of from 0.01 to less than 0.25; type 2, wherein (q/n) is in the range of from 0.25 to less than 0.35; type 3 wherein (q/n) is in the range of from 0.35 to less than 0.50; or type 4 wherein (q/n) is in the range of from 0.50 to less than 1.00. In the foregoing classification step (ix) hiding data is classified on the basis of a degree of steepness or shallowness of the slope of the measured hiding data. By way of example, the measured hiding data in FIG. 9 shows a shallow slope and q/n is 0.55. Thus, such hiding data would be classified as type 4 hiding data. By way illustration FIG. 10 shows how various types of hiding data, i.e., types 1, 2, 3 and 4 would typically appear in a graphical format.

Step (x) of the method of characterizing hiding of a coating composition includes selecting one or more fitting equations applicable for the type 1 hiding data, type 2 hiding data, type 3 hiding data or type 4 hiding data, wherein the fitting equations define a relationship between (y) and (x), the (y) being a fitted color difference that corresponds to the (x), which is a fitted thickness on a fitted curve generated by the one or more fitting equations. Once the hiding data is classified, in the foregoing step (x), a fitting equation that is most applicable for the type of hiding data (type 1, type 2, type 3 or type 4) is selected from a library of various stored fitting equations.

Figure 11:
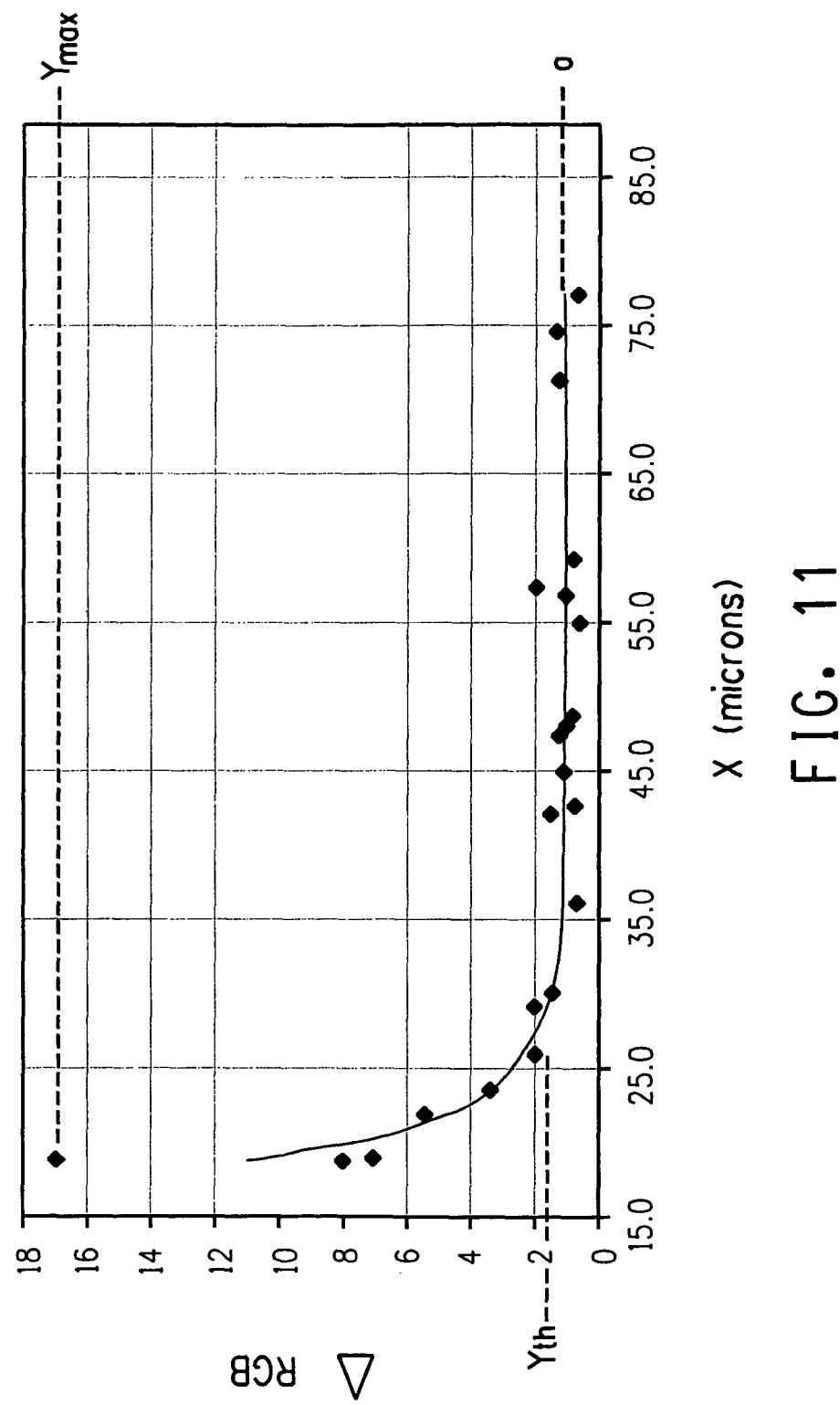

When the hiding data are the type 4 hiding data, the fitted equation is of the formula:

$$y = a + b\exp(-c^*x) \qquad (3)$$

wherein a, b and c are fitting parameters. By way of example, FIG. 11 having steep slope illustrates the fitted curve obtained by using the foregoing equation 3 wherein the q/n is 0.27 and thus classified as a type 2. In FIG. 11 fitting parameter 'a' is the value of 'y' in equation 3 at an asymptote point whereas $Y_{max}$ would be the highest color difference ΔRGB. In FIG. 11, one can readily observe the fitted curve that would be generated by the fitting equation 3.

The fitting parameters a, b and c of the foregoing fitting equation 3 are determined by the steps comprising:

(a) randomly assigning numerical values $a^1$, $b^1$ and $c^1$ to the fitting parameters;

(b) inserting the measured $X_1$ to the $X_n$ into the fitting equation (3) to compute initial fitted $y_1^1$ to $y_n^1$ generated by the fitting equation (3) inserted with the randomly assigned numerical values $a^1$, $b^1$ and $c^1$;

(c) determining error ϵ between the initial fitted $y_1^1$ to $y_n^1$ and the measured $Y_1$ to $Y_n$ by using the equation of formula:

$$\varepsilon = \sum_{i=1}^{n}(Y_i - y_i^1)^2, \text{ and} \qquad (4)$$

(d) deriving the fitting parameters a, b and c by iteratively modifying the $a^1$, $b^1$ and $c^1$ by means of error minimizing equations until a change in the error ϵ between two successive iterations ranges from 1 to $10^{-10}$.

The aforementioned minimizing equations for the type 4 hiding data are of the formulas:

$$a^{(m+1)} = a^m + k_1 \sum_{i=1}^{n}(Y_i - y_i^m), \qquad (5)$$

$$b^{(m+1)} = b^m + k_2 \sum_{i=1}^{n}(Y_i - y_i^m)\exp(-c^m X_i), \text{ and;} \qquad (6)$$

$$c^{(m+1)} = c^m - k_3 b^m \sum_{i=1}^{n} X_i(Y_i - y_i^m)\exp(-c^m X_i), \qquad (7)$$

wherein when m=1, the randomly assigned numerical values are $a^1$, $b^1$ and $c^1$, the m and m+1 being consecutive iterations, and wherein:

the $k_1$ is $1/(22)^2$, the $k_2$ is $1 / \left[\sum_{i=1}^{n} \exp(-c^m X_i)\right]^2$ and the $k_3$ is $1 / \left[-b \sum_{i=1}^{n} X_i \exp(-c^m X_i)\right]^2$.

When the hiding data are the type 1 hiding data, the fitted equation is of the formula:

$$x = -(1/c)\log_e[(y-a)/b] \qquad (8)$$

wherein a, b and c are fitting parameters, wherein the fitting parameter 'a' ranges from a lowest the measured value $Y_{lw}$ to an average, preferably an arithmetic average of measured the $Y_q$ to $Y_n$ and the fitting parameters 'b' and 'c' are determined by the steps comprising:

(a) randomly assigning numerical values $b^1$ and $c^1$ to the fitting parameters;

(b) inserting the measured $Y_1$ to the $Y_{q-1}$ into the fitting equation (8) to compute initial fitted $x_1^1$ to $x_{q-1}^1$ generated by the fitting equation (8) inserted with the randomly assigned numerical values $b^1$ and $c^1$;

(c) determining error ϵ between the initial fitted $x_1^1$ to $x_{q-1}^1$ and the measured $X_1$ to $X_{q-1}$ by using the equation of formula:

$$\varepsilon = \sum_{i=1}^{q-1}(X_i - x_i^1)^2, \text{ and} \qquad (9)$$

(d) deriving the fitting parameters b and c by iteratively modifying the $b^1$ and $c^1$ by means of error minimizing equations until a change in the error $\epsilon$ between two successive iterations ranges from 1 to $10^{-10}$.

The aforementioned minimizing equations for the type 1 hiding data are of the formulas:

$$b^{(m+1)} = b^m + (k_2/b^m c^m) \sum^{q-1} (X_i - x_i^m) \text{ and} \tag{11}$$

$$c^{(m+1)} = c^m - k_3/(c^m)^2 \sum^{q-1} \log_e\{(Y_i - a)/(b^m)\}(X_i - x_i^m) \tag{12}$$

wherein when m=1, the randomly assigned numerical values are $b^1$ and $c^1$, the m and m+1 being consecutive iterations, and wherein:

$$k_2 = \left\{1 \Big/ \left(\sum^{q-1} (1/b^m c^m)\right)\right\}^2 \text{ and}$$

$$k_3 = \left[\sum^n \{(c^m)^2 / (\log_e((Y_i - a)/(b^m)))\}\right]^2.$$

When the hiding data are the types 2 or 3 hiding data, the fitted equation is of the formula:

$$x = -(1/c^\#)\log_e[(y-a)/b^\#], \text{ and} \tag{13}$$

wherein for the measured $Y_1$ to $Y_n$ the fitted equation is of the formula:

$$y = a + b^@ \exp(-c^@ * x) \tag{14}$$

wherein a, $b^\#$, $b^@$ and $c^\#$ and $c^@$ are fitting parameters, wherein fitting parameter 'a' ranges from a lowest the measured value $Y_{lw}$ to an average, preferably an arithmetic average, of measured the $Y_q$ to $Y_n$; and the $b^\#$ and $C^\#$ parameters of the equation (13) are determined by the steps comprising:

(a) randomly assigning numerical values $b^1$ and $c^1$ to the fitting parameters;

(b) inserting the measured $Y_1$ to the $Y_{q-1}$ into the fitting equation (13) to compute initial fitted $x_1^1$ to $x_{q-1}^1$ generated by the fitting equation (13) inserted with the randomly assigned numerical values $b^1$ and $c^1$;

(c) determining error $\epsilon$ between the initial fitted $x_1^1$ to $x_{q-1}^1$ and the measured $X_1$ to $X_{q-1}$ by using the equation of formula:

$$\varepsilon = \sum^{q-1} (X_i - x_i^1)^2, \text{ and} \tag{15}$$

(d) deriving the fitting parameters $b^\#$ and $c^\#$ by iteratively modifying the $b^1$ and $c^1$ by means of error minimizing equations until a change in the error $\epsilon$ between two successive iterations ranges from 1 to $10^{-10}$.

The aforementioned minimizing equations for the types 2 or 3 hiding data are of the formulas utilizing equation (13) are:

$$b^{\#(m+1)} = b^{\#m} + (k_2/b^{\#m} c^{\#m}) \sum^{q-1} (X_i - x_i^m) \text{ and} \tag{16}$$

$$c^{\#(m+1)} = c^{\#m} - k_3/(c^{\#m})^2 \sum^{q-1} \log_e\{(Y_i - a)/(b^{\#m})\}(X_i - x_i^m) \tag{17}$$

wherein when m=1, the randomly assigned numerical values are $b^1$ and $c^1$, the m and m+1 being consecutive iterations, and wherein:

$$k_2 = \left\{1 \Big/ \left(\sum^{q-1} (1/b^{\#m} c^{\#m})\right)\right\}^2 \text{ and}$$

$$k_3 = \left[\sum^n \{(c^{\#m})^2 / (\log_e((Y_i - a)/(b^{\#m})))\}\right]^2.$$

In aforementioned equation (14), the $b^@$ and $c^@$ parameters are determined by the steps comprising:

(a) assigning numerical values $b^\#$ and $c^\#$ to the fitting parameters;

(b) inserting the measured $X_1$ to the $X_n$ into the fitting equation (14) to compute initial fitted $y_1^\#$ to $y_n^\#$ generated by the fitting equation (14) inserted with the assigned numerical values $b^\#$ and $c^\#$;

(c) determining error $\epsilon$ between the initial fitted $y_1^\#$ to $y_n^\#$ and the measured $Y_1$ to $Y_n$ by using the equation of formula:

$$\varepsilon = \sum^n (Yi - yi^\#)^2, \text{ and} \tag{18}$$

(d) deriving the fitting parameters $b^@$ and $c^@$ by iteratively modifying the $b^\#$ and $c^\#$ by means of error minimizing equations until a change in the error $\epsilon$ between two successive iterations ranges from 1 to $10^{-10}$.

The aforementioned minimizing equations for the types 2 or 3 hiding data are of the formulas utilizing equation (14) are:

$$a^{(m+1)} = a^m + k_1 \sum^n (Y_i - y_i^m), \tag{19}$$

$$b^{(m+1)} = b^m + k_2 \sum^n (Y_i - y_i^m)\exp(-c^m X_i), \text{ and}; \tag{20}$$

$$c^{(m+1)} = c^m - k_3 b^m \sum^n x_i(Y_i - y_i^m)\exp(-c^m X_i), \tag{21}$$

wherein when m=1, the randomly assigned numerical values are $a^1$, $b^1$ and $c^1$, the m and m+1 being consecutive iterations, and wherein:

the $k_1$ is $1/(22)^2$, n the $k_2$ is $1 \Big/ \left[\sum \exp(-c^m X_i)\right]^2$ and the $k_3$ is $1 \Big/ \left[-b \sum^n X_i \exp(-c^m X_i)\right]^2$.

Step (xi) of the method of characterizing hiding of a coating composition includes fitting said one or more selected fitting equations to match paired measured $(X_1, Y_1)$ to paired measured $(X_n, Y_n)$, wherein the fitted curve has a fitted baseline value of $y_b$ at an asymptote of said fitted curve.

Step (xii) of the method of characterizing hiding of a coating composition includes selecting a fitted threshold value $y_{th}$ above the fitted baseline value $y_b$, wherein the fitted threshold value $y_{th}$ is suited for the type 1 hiding data, type 2 hiding data, type 3 hiding data or type 4 hiding data.

In the foregoing step (xii) when the hiding data are the type 3 or type 4 hiding data, the fitted threshold value $y_{th}$ is 1 when $(Y_{max} - a)$ is either more than 15 or the $Y_{max}$ is in the range of 10 to 255. In all other cases when $(Y_{max} - a)$ is either less than 15 and said $Y_{max}$ is less than 10, the fitted threshold value $y_{th}$ is expressed by the formula:

$$0.1*(Y_{max}/a)*\text{Log }10\{(Y_{max}-a)/(a+1)\} \quad (22)$$

provided the value expressed by the formula (19) is more than 0.3 (as shown in FIG. 11 $y_{th}$ is about 1.5); or the fitted threshold value $y_{th}$ is 0.3 if value expressed by the formula (22) is equal to or less than 0.3.

Figure 12:
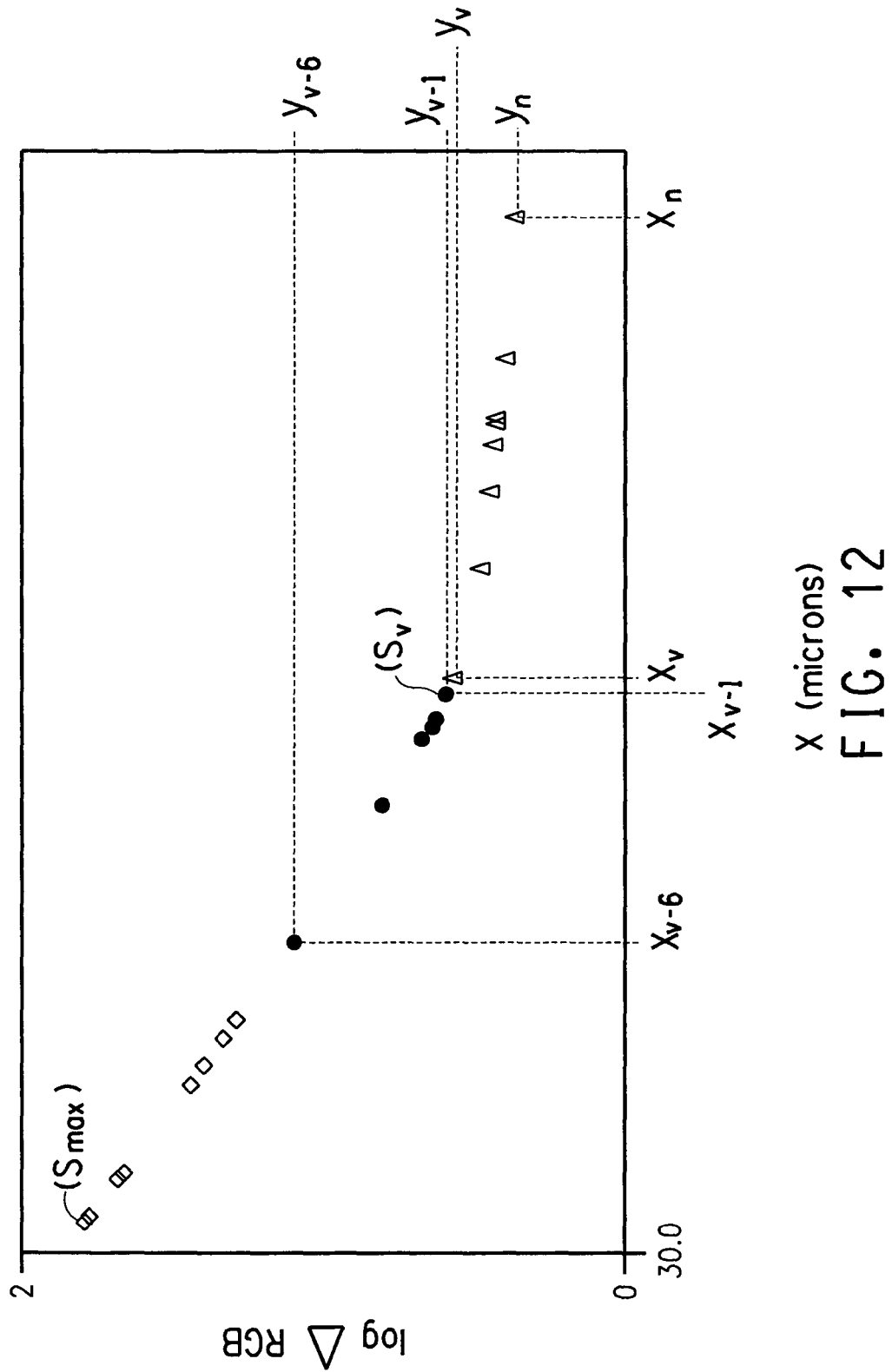

In the foregoing step (xii) and as shown in FIG. 12 when the hiding data are the type 1 or type 2 hiding data, the fitted threshold value $y_{th}$ is determined by the steps comprising:

(a) computing slope $S_x$ by using the following formula:

$$S_x = d[\text{Log }\{y\}]/dx = \{-b*c*\exp(-cx)\}/[\text{Log }\{a+b*\exp(-cx)\}]; \quad (23)$$

Figure 13:
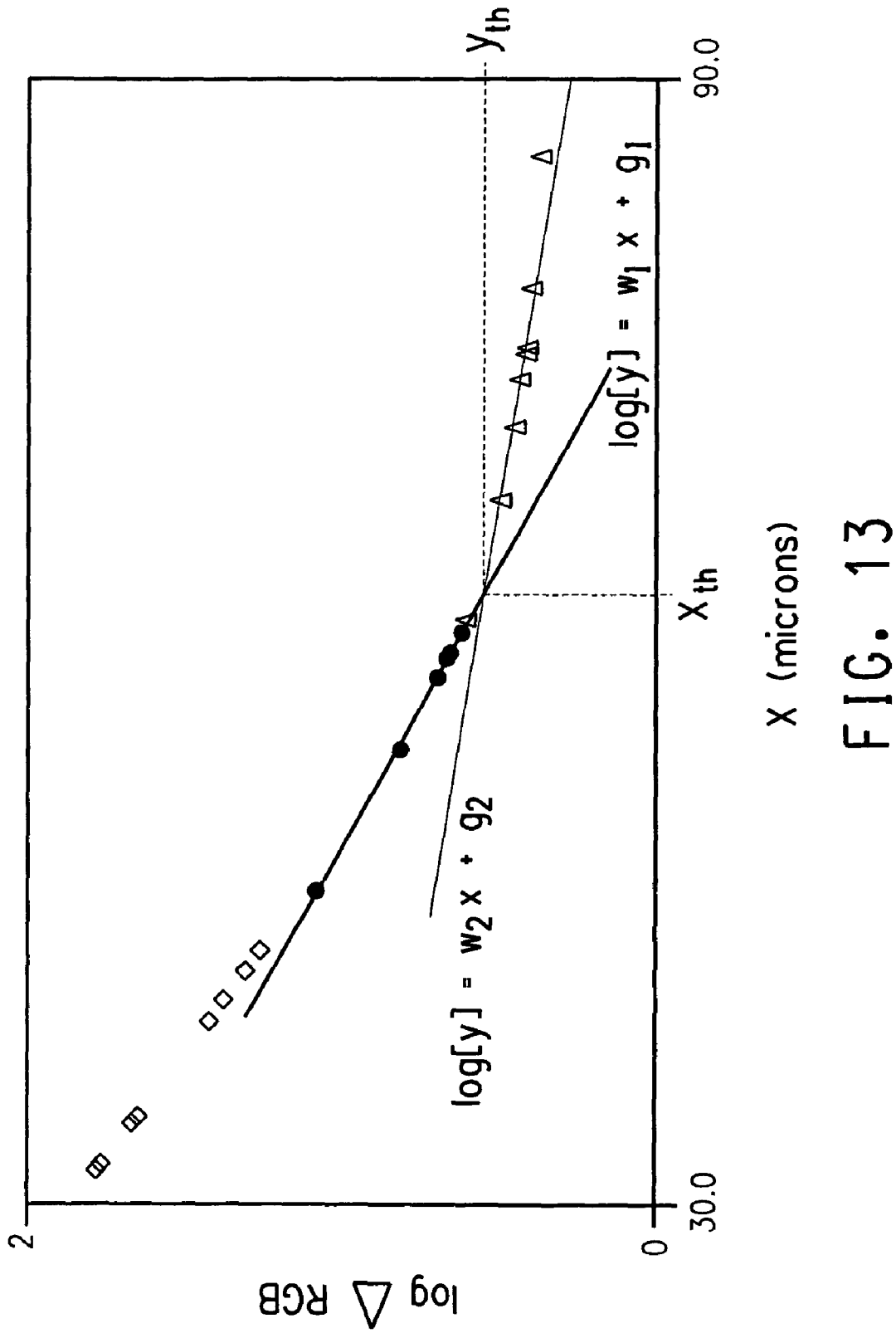

(b) selecting slope $S_{max}$ at the measured thickness $X_1$;

(c) selecting first measured thickness $X_v$ at less than half of the slope $S_x$;

(d) establishing a first range of the fitted $y_{v-6}$ to $y_{v-1}$ on a fitted $\log_{10}$ curve that correspond to measured thicknesses ranging from $X_{v-6}$ to $X_{v-1}$ and a second range of the fitted $y_v$ to the $y_n$ on the fitted $\log_{10}$ curve that correspond to measured thicknesses ranging from the $X_v$ to $X_n$;

As shown in FIG. 13 in step (e) inserting the fitted $y_{v-6}$ to $y_{v-1}$ and the from $X_{v-6}$ to $X_{v-1}$ of the first range in the following formula:

$$\text{Log}_{10} y = w_1 x + g_1 \quad (24)$$

wherein the $w_1$ is a slope of a first straight line computed by the formula (24) and the $g_1$ is a value of y when x=0 in the formula (24);

(f) inserting the fitted $y_v$ to $y_n$ and the from $X_v$ to $X_n$ of the second range in the following formula:

$$\text{Log}_{10} y = w_2 x + g_2 \quad (25)$$

wherein the $w_2$ is a slope of a second straight line computed by the formula (22) and the $g_2$ is a value of y when x=0 in the formula (25); and (g) computing a point of intersection of the first and the second straight lines obtained though the formula:

$$\text{Log}_{10} y_{th} = (w_2 g_1 - w_1 g_2)/(w_2 - w_1) \quad (26).$$

Step (xii) of the method of characterizing hiding of a coating composition includes locating a hiding thickness $x_h$ of the coating composition that corresponds to the fitted threshold value $y_{th}$ on the fitted curve. One can readily note in FIG. 13 the point $x_h$.

The coating composition suitable use in the present method can be a refinish automotive paint, OEM automotive paint, architectural paint, or an industrial paint.

What is claimed is:

1. A method of characterizing hiding of a coating composition, said method comprising:
   (i) applying a monotonic layer of said coating composition over a test pattern affixed to a hiding test panel to produce a monotonic coating thereon;
   (ii) sequentially uniformly illuminating target areas $P_1$ to $P_n$ of said monotonic coating, each said target area comprising a light portion and a dark portion;
   (iii) sequentially directing reflections of said target areas $P_1$ to $P_n$ to a photosensitive device for acquiring:
      (a) intensities $lr_1$ to $lr_n$, $lg_1$ to $lg_n$ and $lb_1$ to $lb_n$ of said light portions of said areas $P_1$ to $P_n$, and
      (b) intensities $dr_1$ to $dr_n$, $dg_1$ to $dg_n$ and $db_1$ to $db_n$ of said dark portions said areas $P_1$ to $P_n$;
   (iv) sequentially measuring applied measured thicknesses $X_1$ to $X_n$ of said monotonic coating at locations that respectively correspond to said target areas $P_1$ to $P_n$;
   (v) sequentially computing measured $Y_1$ to $Y_n$ at said target areas $P_1$ to $P_n$ by using the formula:

$$[(lr_i - dr_i)^2 + (lg_i - dg_i)^2 + (lb_i - db_i)^2]^{0.5} \quad (1)$$

wherein i ranges from 1 to n, and said measured $Y_1$ to $Y_n$ are measured ΔRGBs;
   (vi) storing on a computing device hiding data comprising said measured $Y_1$ to $Y_n$ and said applied thicknesses $X_1$ to $X_n$;
   (vii) determining a threshold measured $Y_{th}$ by using the formula:

$$\text{measured } Y_{th} = \text{Log}_e(\text{measured } Y_{max}), \quad (2)$$

said measured $Y_{max}$ being the maximum value within the range of said measured $Y_1$ to $Y_n$;
   (viii) sequentially comparing said measured $Y_1$ through $Y_n$ to identify first measured $Y_q$ that is less than measured $Y_{th}$ wherein q falls within said range 1 to n;
   (ix) computing a ratio (q/n) to classify said hiding data, wherein said is classified as:
      (i) type 1 hiding data when said ratio is in the range of 0.01 to less than 0.25,
      (j) type 2 hiding data when said ratio is in the range of 0.25 to less 0.35,
      (k) type 3 hiding data when said ratio is in the range of 0.35 to less 0.50, or
      (l) type 4 hiding data when said ratio is in the range of 0.50 to 1.00;
   (x) selecting one or more fitting equations applicable for said type 1 hiding data, type 2 hiding data, type 3 hiding data or type 4 hiding data, wherein said fitting equations define a relationship between (y) and (x), said (y) being a fitted color difference that corresponds to said (x), which is a fitted thickness on a fitted curve generated by said one or more fitting equations;
   (xi) fitting said one or more selected fitting equations to match paired measured $(X_1, Y_1)$ to paired measured $(X_n, Y_n)$, wherein said fitted curve has a fitted baseline value of $y_b$ at an asymptote of said fitted curve;
   (xii) selecting a fitted threshold value $y_{th}$ above said fitted baseline value $y_b$, wherein said fitted threshold value $y_{th}$ is suited for said type 1 hiding data, type 2 hiding data, type 3 hiding data or type 4 hiding data; and
   (xiii) locating a hiding thickness $x_h$ of said coating composition that corresponds to said fitted threshold value $y_{th}$ on said fitted curve.

2. The method of claim 1 wherein when said hiding data are said type 4 hiding data, said fitted equation is of the formula:

$$y = a + b \exp(-c*x) \quad (3)$$

wherein a, b and c are fitting parameters.

3. The method of claim 2 wherein said a, b and c are determined by the steps comprising:
   (a) randomly assigning numerical values $a^1$, $b^1$ and $c^1$ to said fitting parameters;
   (b) inserting said measured $X_1$ to said $X_n$ into said fitting equation (3) to compute initial fitted $y_1^1$ to $y_n^1$ generated by said fitting equation (3) inserted with said randomly assigned numerical values $a^1$, $b^1$ and $c^1$;
   (c) determining error ε between said initial fitted $y_1^1$ to $y_n^1$ and said measured $Y_1$ to $Y_n$, by using the equation of formula:

$$\varepsilon = \sum_{i}^{n}(Y_i - y_i^1)^2, \text{ and} \quad (4)$$

(d) deriving said fitting parameters a, b and c by iteratively modifying said $a^1$, $b^1$ and $c^1$ by means of error minimizing equations until a change in said error $\epsilon$ between two successive iterations ranges from 1 to $10^{-10}$.

4. The method of claim 3 wherein said minimizing equations are of the formulas:

$$a^{(m+1)} = a^m + k_1 \sum_{i=1}^{n}(Y_i - y_i^m), \quad (5)$$

$$b^{(m+1)} = b^m + k_2 \sum_{i=1}^{n}(Y_i - y_i^m)\exp(-c^m X_i), \text{ and}; \quad (6)$$

$$c^{(m+1)} = c^m - k_3 b^m \sum_{i=1}^{n} x_i(Y_i - y_i^m)\exp(-c^m X_i), \quad (7)$$

wherein when m=1, said randomly assigned numerical values are $a^1$, $b^1$ and $c^1$, said m and m+1 being consecutive iterations, and wherein:

said $k_1$ is $1/(22)^2$, said $k_2$ is $1 / \left[\sum_{i=1}^{n} \exp(-c^m X_i)\right]^2$ and said $k_3$ is $1 / \left[-b \sum_{i=1}^{n} X_i \exp(-c^m X_i)\right]^2$.

5. The method of claim 1 wherein when said hiding data are said type 1 hiding data, said fitted equation is of the formula:

$$x = -(1/c)\log_e[(y-a)/b] \quad (8)$$

wherein a, b and c are fitting parameters.

6. The method of claim 5 wherein said fitting parameter a ranges from a lowest said measured value $Y_{lw}$ to an average of measured said $Y_q$ to $Y_n$.

7. The method of claim 5 wherein said fitting parameter a ranges from a lowest said measured value $Y_{lw}$ to an arithmetic average of measured said $Y_q$ to $Y_n$.

8. The method of claim 6 or 7 wherein said b and c are determined by the steps comprising:
   (a) randomly assigning numerical values $b^1$ and $c^1$ to said fitting parameters;
   (b) inserting said measured $Y_1$ to said $Y_{q-1}$ into said fitting equation (8) to compute initial fitted $x_1^1$ to $x_{q-1}^1$ generated by said fitting equation (8) inserted with said randomly assigned numerical values $b^1$ and $c^1$;
   (c) determining error $\epsilon$ between said initial fitted $x_1^1$ to $x_{q-1}^1$ and said measured $X_1$ to $X_{q-1}$ by using the equation of formula:

$$\varepsilon = \sum_{i=1}^{q-1}(X_i - x_i^1)^2, \text{ and} \quad (9)$$

(d) deriving said fitting parameters b and c by iteratively modifying said $b^1$ and $c^1$ by means of error minimizing equations until a change in said error $\epsilon$ between two successive iterations ranges from 1 to $10^{-10}$.

9. The method of claim 8 wherein said minimizing equations are of the formulas:

$$b^{(m+1)} = b^m + (k_2/b^m c^m)\sum_{i=1}^{q-1}(X_i - x_i^m) \text{ and} \quad (11)$$

$$c^{(m+1)} = c^m - k_3/(c^m)^2 \sum_{i=1}^{q-1} \log_e\{(Y_i - a)/(b^m)\}(X_i - x_i^m) \quad (12)$$

wherein when m=1, said randomly assigned numerical values are $b^1$ and $c^1$, said m and m+1 being consecutive iterations, and wherein:

$$k_2 = \left\{1 / \left(\sum_{i=1}^{q-1}(1/b^m c^m)\right)\right\}^2 \text{ and}$$

$$k_3 = \left[\sum_{i=1}^{n}\{(c^m)^2/(\log_e((Y_1 - a)/(b^m)))\}\right]^2.$$

10. The method of claim 1 wherein when said hiding data are said type 2 or said type 3 hiding data for said measured $Y_1$ to $Y_o$, said fitted equation is of the formula:

$$x = -(1/c^\#)\log_e[(y-a)/b^\#], \text{ and} \quad (13)$$

wherein for said measured $Y_1$ to Yn said fitted equation is of the formula:

$$y = a + b^@ \exp(-c^@ *x) \quad (14)$$

wherein a, $b^\#$, $b^@$ and $c^\#$ and $c^@$ are fitting parameters.

11. The method of claim 10 wherein said fitting parameter a ranges from a lowest said measured value $Y_{lw}$ to an average of measured said $Y_q$ to $Y_n$.

12. The method of claim 10 wherein said fitting parameter a ranges from a lowest said measured value $Y_{lw}$ to an arithmetic average of measured said $Y_q$ to $Y_n$.

13. The method of claim 11 or 12 wherein said $b^\#$ and $c^\#$ are determined by the steps comprising:
   (a) randomly assigning numerical values $b^1$ and $c^1$ to said fitting parameters;
   (b) inserting said measured $Y_1$ to said $Y_{q-1}$ into said fitting equation (13) to compute initial fitted $x_1^1$ to $x_{q-1}^1$ generated by said fitting equation (13) inserted with said randomly assigned numerical values $b^1$ and $c^1$;
   (c) determining error $\epsilon$ between said initial fitted $x_1^1$ to $x_{q-1}^1$ and said measured $X_1$ to $X_{q-1}$ by using the equation of formula:

$$\varepsilon = \sum_{i=1}^{q-1}(X_i - x_i^1)^2, \text{ and} \quad (15)$$

(d) deriving said fitting parameters $b^\#$ and $c^\#$ by iteratively modifying said $b^1$ and $c^1$ by means of error minimizing equations until a change in said error $\epsilon$ between two successive iterations ranges from 1 to $10^{-10}$.

14. The method of claim 13 wherein said minimizing equations are of the formulas:

$$b^{\#(m+1)} = b^{\#m} + (k_2/b^{\#m} c^{\#m})\sum_{i=1}^{q-1}(X_i - x_i^m) \text{ and} \quad (16)$$

$$c^{\#(m+1)} = c^{\#m} - k_3/(c^{\#m})^2 \sum_{i=1}^{q-1} \log_e\{(Y_i - a)/(b^{\#m})\}(X_i - x_i^m) \quad (17)$$

wherein when m=1, said randomly assigned numerical values are $b^1$ and $c^1$, said m and m+1 being consecutive iterations, and wherein:

$$k_2 = \left\{1 \bigg/ \left[\sum_{}^{q-1}(1/b^{\#m}c^{\#m})\right]\right\}^2 \text{ and}$$

$$k_3 = \left[\sum_{}^{n}\left\{(c^{\#m})^2 / (\log_e((Y_i-a)/(b^{\#m}))\right\}\right]^2.$$

15. The method of claim 11 or 12 wherein said $b^@$ and $c^@$ are determined by the steps comprising:
   (a) assigning numerical values $b^\#$ and $c^\#$ to said fitting parameters;
   (b) inserting said measured $X_1$ to said $X_n$ into said fitting equation (14) to compute initial fitted $y_1^\#$ to $y_n^\#$ generated by said fitting equation (14) inserted with said assigned numerical values $b^\#$ and $c^\#$;
   (c) determining error $\epsilon$ between said initial fitted $y_1^\#$ to $y_n^\#$ and said measured $Y_1$ to $Y_n$ by using the equation of formula:

$$\varepsilon = \sum_{}^{n}(Y_i - y_i^\#)^2, \text{ and} \qquad (18)$$

(d) deriving said fitting parameters $b^@$ and $c^@$ by iteratively modifying said $b^\#$ and $c^\#$ by means of error minimizing equations until a change in said error $\epsilon$ between two successive iterations ranges from 1 to $10^{-10}$.

16. The method of claim 15 wherein said minimizing equations are of the formulas:

$$a^{(m+1)} = a^m + k_1 \sum_{}^{n}(Y_i - y_i^m), \qquad (19)$$

$$b^{(m+1)} = b^m + k_2 \sum_{}^{n}(Y_i - y_i^m)\exp(-c^m X_i), \text{ and;} \qquad (20)$$

$$c^{(m+1)} = c^m - k_3 b^m \sum_{}^{n} x_i(Y_i - y_i^m)\exp(-c^m X_i), \qquad (21)$$

wherein when m=1, said randomly assigned numerical values are $a^1$, $b^1$ and $c^1$, said m and m+1 being consecutive iterations, and wherein:

said $k_1$ is $1/(22)^2$, said $k_2$ is $1\bigg/\left[\sum_{}^{n}\exp(-c^m X_i)\right]^2$ and said $k_3$ is $1\bigg/\left[-b\sum_{}^{n}X_i\exp(-c^m X_i)\right]^2$.

17. The method of claim 1 wherein in said step (xii) when said hiding data are said type 3 or type 4 hiding data, said fitted threshold value $y_{th}$ is 1 when ($Y_{max}$–a) is either more than 15 or said $Y_{max}$ is in the range of 10 to 255.

18. The method of claim 1 wherein in said step (xii) when said hiding data are said type 3 or type 4 hiding data and when ($Y_{max}$–a) is either less than 15 and said $Y_{max}$ is less than 10;
   (a) said fitted threshold value $y_{th}$ is expressed by the formula:

$$0.1*(Y_{max}/a)*\text{Log}_{10}\{(Y_{max}-a)/(a+1)\} \qquad (22)$$

provided value expressed by said formula (19) is more than 0.3; or
   (b) said fitted threshold value $y_{th}$ is 0.3 if value expressed by said formula (22) is equal to or less than 0.3.

19. The method of claim 1 wherein in said step (xii) when said hiding data are said type 1 or type 2 hiding data said fitted threshold value $y_{th}$ is determined by the steps comprising
   (a) computing slope $S_x$ by using the following formula:

$$S_x = d[\text{Log}\{y\}]/dx = \{-b*c*\exp(-cx)\}/[\text{Log}\{a+b*\exp(-cx)\}]; \qquad (23)$$

(b) selecting slope $S_{max}$ at said measured thickness $X_1$;
   (c) selecting first measured thickness $X_v$ at less than half of said slope $S_x$;
   (d) establishing a first range of said fitted $y_{v-6}$ to $y_{v-1}$ on a fitted $\log_{10}$ curve that correspond to measured thicknesses ranging from $X_{v-6}$ to $X_{v-1}$ and a second range of said fitted $y_v$ to said $y_n$ on said fitted $\log_{10}$ curve that correspond to measured thicknesses ranging from said $X_v$ to $X_n$;
   (e) inserting said fitted $y_{v-6}$ to $y_{v-1}$ and said from $X_{v-6}$ to $X_{v-1}$ of said first range in the following formula:

$$\text{Log}_{10}y = w_1 x + g_1 \qquad (24)$$

wherein said $w_1$ is a slope of a first straight line computed by said formula (24) and said $g_1$ is a value of y when x=0 in said formula (24);
   (f) inserting said fitted $y_v$ to $y_n$ and said from $X_v$ to $X_n$ of said second range in the following formula:

$$\text{Log}_{10}y = w_2 x + g_2 \qquad (25)$$

wherein said $w_2$ is a slope of a second straight line computed by said formula (22) and said $g_2$ is a value of y when x=0 in said formula (25); and
   (g) computing a point of intersection of said first and said second straight lines obtained though the formula:

$$\text{Log}_{10}y_{th} = (w_2 g_1 - w_1 g_2)/(w_2 - w_1) \qquad (26).$$

20. The method of claim 1 wherein said coating composition is a refinish automotive paint, OEM automotive paint, architectural paint, or an industrial paint.

* * * * *